US012232884B2

(12) United States Patent
Kwak et al.

(10) Patent No.: US 12,232,884 B2
(45) Date of Patent: Feb. 25, 2025

(54) ROBOT FOR MIMICKING POSTURE OF USER AND REAL-TIME POSTURE MONITORING SYSTEM INCLUDING THE SAME

(71) Applicant: Morethings Co., Ltd., Yongin-si (KR)

(72) Inventors: Jae Kyung Kwak, Yongin-si (KR); Ji Won Oh, Gwangju-si (KR); Hwan Il Park, Seoul (KR); Jeong Min Han, Seoul (KR)

(73) Assignee: Morethings Co., Ltd., Yongin-si (KR)

( * ) Notice: Subject to any disclaimer, the term of this patent is extended or adjusted under 35 U.S.C. 154(b) by 882 days.

(21) Appl. No.: 17/339,321

(22) Filed: Jun. 4, 2021

(65) Prior Publication Data
US 2021/0330248 A1 Oct. 28, 2021

Related U.S. Application Data

(63) Continuation of application No. PCT/KR2018/015350, filed on Dec. 5, 2018.

(30) Foreign Application Priority Data

Dec. 5, 2018 (KR) .................. 10-2018-0155519

(51) Int. Cl.
A61B 5/00 (2006.01)
A61B 5/0205 (2006.01)
(Continued)

(52) U.S. Cl.
CPC .......... *A61B 5/4561* (2013.01); *A61B 5/0205* (2013.01); *A61B 5/0261* (2013.01); *A61B 5/1116* (2013.01); *A61B 5/7203* (2013.01); *A61B 5/725* (2013.01); *A61B 5/7264* (2013.01); *A61B 5/743* (2013.01); *A61B 2560/04* (2013.01);
(Continued)

(58) Field of Classification Search
CPC ... A61B 5/0205; A61B 5/0261; A61B 5/1116; A61B 5/4561; A61B 5/486; A61B 5/7203; A61B 5/725; A61B 5/7264; A61B 5/743; A61B 2560/04; B25J 9/102; B25J 9/126; B25J 9/1697; B25J 11/0005; B25J 11/009
See application file for complete search history.

(56) References Cited

U.S. PATENT DOCUMENTS 5,570,301 A * 10/1996 Barrus .................. G01G 19/44
702/41
2018/0075403 A1* 3/2018 Mascorro Medina .......................
B25J 9/1697
2020/0405245 A1* 12/2020 Tezuka .................. A61B 5/486

FOREIGN PATENT DOCUMENTS

JP 2006-088276 A 4/2006
KR 20-0441761 Y1 9/2008
(Continued)

OTHER PUBLICATIONS

Translation of KR 101546249 (Year: 2015).*
(Continued)

*Primary Examiner* — Devin B Henson
(74) *Attorney, Agent, or Firm* — Studebaker & Brackett PC

(57) ABSTRACT

Disclosed are a robot that may allow a user to monitor a state and a posture of the user in real time to perceive a state of health and the posture and receive useful contents that are helpful, and effectively help the health and correction of the posture of the user, and a real-time posture monitoring method.

14 Claims, 11 Drawing Sheets

(51) Int. Cl.
    *A61B 5/026* (2006.01)
    *A61B 5/11* (2006.01)
    *B25J 9/10* (2006.01)
    *B25J 9/16* (2006.01)
    *B25J 11/00* (2006.01)
    *B25J 9/12* (2006.01)
(52) U.S. Cl.
    CPC ................ *B25J 9/102* (2013.01); *B25J 9/126* (2013.01); *B25J 9/1697* (2013.01); *B25J 11/0005* (2013.01)

(56) References Cited

FOREIGN PATENT DOCUMENTS

| | | |
|---|---|---|
| KR | 10-1419430 B1 | 7/2014 |
| KR | 10-1485894 B1 | 1/2015 |
| KR | 10-1546249 B1 | 8/2015 |
| KR | 10-2017-0056232 A | 5/2017 |
| KR | 10-1866883 B1 | 6/2018 |
| KR | 10-2018-0092456 A | 8/2018 |

OTHER PUBLICATIONS

International Search Report issued in PCT/KR2018/015350; mailed Sep. 3, 2019.
International Preliminary Report on Patentability and Written Opinion issued in PCT/KR2018/015350; issued Jun. 8, 2021.
Office Action issued in KR 10-2018-0155519; mailed by the Korean Intellectual Property Office on Mar. 14, 2020.

\* cited by examiner (1)

(2)

(3)

(1)

(2)

(1)

(2)

(1)

(2)

ROBOT FOR MIMICKING POSTURE OF USER AND REAL-TIME POSTURE MONITORING SYSTEM INCLUDING THE SAME

CROSS-REFERENCE TO RELATED APPLICATIONS

The present application is a continuation of International Patent Application No. PCT/KR2018/015350, filed on Dec. 5, 2018, which is based upon and claims the benefit of priority to Korean Patent Application No. 10-2018-0155519 filed on Dec. 5, 2018. The disclosures of the above-listed applications are hereby incorporated by reference herein in their entirety.

BACKGROUND

Embodiments of the inventive concept described herein relate to a robot for mimicking a posture of a user, and a method for monitoring a posture of a user by using the same.

In recent years, as people have spent more times for performing operations with poor postures during works or at homes, the number of patients having spine diseases has increased. In particular, in contrast to the correct postures, the poor postures cause misalignment of the vertebrae, the thoracic vertebrae, and the cervical vertebrae due to the changes in the inclinations of the pelvises, and thus cause the thoracic kyphosis, the round shoulders, the head forward positions, and the like.

Statistically, in Korea, the number of the patients of spine diseases was 12.6 million in one year of 2015 (increased by 3.65 million for 7 years), and the medical service fees spent for the treatments of the spine diseases amounted to 3.8755 trillion.

Accordingly, various correction devices for correcting misalignment of joints of the spines due to poor postures have been released. However, the corrections using the devices are not preferable because they are physical and compulsory corrections and correspond to following-up measures.

Meanwhile, the modern people are suffering from various spine diseases and stresses due to businesses as well.

Accordingly, the above-described problems may be solved by a real-time posture monitoring system that may allow a user to intuitively recognize a state and a posture of the user by monitoring the state and the posture of the user in real time and coach the management of health and correction of the posture.

SUMMARY

Embodiments of the inventive concept provide a robot that may allow a user to monitor a state and a posture of the user in real time to perceive a state of health and the posture and receive useful contents that are helpful, and effectively help the health and correction of the posture of the user, and a real-time posture monitoring method.

The technical objects of the inventive concept are not limited to the above-mentioned ones, and the other unmentioned technical objects will become apparent to those skilled in the art from the following description.

According to an embodiment, a robot for mimicking a posture of a user, the robot includes a case, a camera disposed in the case, and that photographs the user and generate a captured image, a display disposed in the case and that reproduces a display image, and an electronic control unit that communicates with the camera and the display, and the electronic control unit derives heart rate information from the captured image, and changes the display image such that the display image corresponds to the heart rate information.

Then, the camera may acquire light of an infrared ray wavelength band and generates the captured image, and the electronic control unit may derive a blood flow change signal of at least one of a face portion and a neck portion of the user from the captured image, derive a heart rate signal by classifying the blood flow change signal according to a frequency thereof and filtering out a noise signal, and derive the heart rate information from the heart rate signal by using a maximum point extraction algorithm.

Furthermore, the display image may include at least one of a background image, a letter, a number, a symbol, a graph, and an emoji corresponding to the heart rate information, and the electronic control unit may classify a state of the user into any one of a normal heart rate state, a low heart rate state, and a high heart rate state, by using the heart rate information, and the at least one of the background image, the letter, the number, the symbol, the graph, and the emoji corresponding to the heart rate information may be differently expressed according to the state of the user.

Furthermore, the electronic control unit may communicate with a pad that senses a magnitude and a distribution of pressures applied by both feet of the user to generate posture information from a pressure signal, and change the display image such that the display image corresponds to the posture information, the display image may include at least one of a background image, a letter, a number, a symbol, a graph, and an emoji, which correspond to the heart rate information, and at least one of a background image, a letter, a number, a symbol, a graph, and an emoji, which correspond to the posture information, and the at least one of the background image, the letter, the number, the symbol, the graph, and the emoji, which correspond to the heart rate information, and the at least one of the background image, the letter, the number, the symbol, the graph, and the emoji, which correspond to the posture information may be reproduced at the same time or alternately.

Then, the electronic control unit may classify the posture of the user into any one of a correct posture, a poor upper body posture, and a posture with crossed legs, the poor upper body posture may include at least one of a first posture, in which an upper body or a neck of the user is bent to any one of an upper side, a lower side, a left side, and a right side, and a second posture, in which a body of the user is leaned or supported by any one of both legs of user, and the at least one of the background image, the letter, the number, the symbol, the graph, and the emoji corresponding to the posture information may be differently expressed according to the posture of the user.

Then, the robot may further include a first leg and a second leg driven to correspond to the posture information in the posture with the crossed legs, and a first driver that drives the first leg and the second leg, the first driver may include a first motor, a rack gear that moves to one side and an opposite side by the first motor, a first driven gear disposed in the first leg, and a second driven gear disposed in the second leg, the rack gear may move to the one side to be enmeshed with the first driven gear through forward rotation driving of the first motor to rotate the first driven gear, the rack gear may move to the opposite side to be enmeshed with the second driven gear through reverse rotation driving of the first motor to rotate the second driven gear, and axes of rotation of the first driven gear and the second driven gear may be parallel to each other and rotational directions of the first driven gear and the second driven gear are opposite to each other.

Furthermore, the case may include an upper case tilted to correspond to the posture information in the poor upper body posture, and a lower case disposed on a lower side of the upper case, and the robot further includes a second driver that tilts the upper case in at least one of a forward/rearward direction and a leftward/rightward direction.

Then, the second driver may include a first bracket, a (2-1)-th motor that rotates the first bracket, a second bracket, and a (2-2)-th motor that rotates the first bracket, one side of the first bracket may be fixed to the upper case, and an opposite side of the first bracket may interwork with a shaft of the (2-1)-th motor and may be hinge-coupled to the second bracket, and one side of the second bracket may be fixed to the upper case, and an opposite side of the second bracket may interwork with a shaft of the (2-2)-th motor.

Then, the first bracket may rotate such that the upper case is tilted forwards, through forward rotation driving of the (2-1)-th motor, the first bracket rotates such that the upper case is tilted rearwards, through reverse rotation driving of the (2-1)-th motor, the second bracket may rotate such that the upper case is tilted leftwards, through forward rotation driving of the (2-2)-th motor, and the second bracket may rotate such that the upper case is tilted rightwards, through reverse rotation driving of the (2-2)-th motor.

According to another embodiment, a method for monitoring a posture of a user by using a robot includes generating an image captured by photographing a user, through a camera disposed in a case of the robot, reproducing a display image, on a display disposed in the case, deriving heart rate information from the captured image, and changing the display image such that the display image corresponds to the heart rate information.

Then, the camera may acquire light of an infrared ray wavelength band and generates the captured image, and the deriving of the heart rate information may include deriving a blood flow change signal of at least one of a face portion and a neck portion of the user, from the captured image, deriving a heart rate signal by classifying the blood flow change signal according to a frequency thereof and filtering out a noise signal, and deriving the heart rate information from the heart rate signal by using a maximum point extraction algorithm.

Then, the display image may include at least one of a background image, a letter, a number, a symbol, a graph, and an emoji corresponding to the heart rate information, a state of the user may be classified into any one of a normal heart rate state, a low heart rate state, and a high heart rate state, based on the heart rate information, and the at least one of the background image, the letter, the number, the symbol, the graph, and the emoji corresponding to the heart rate information may be differently expressed according to the state of the user.

Furthermore, the robot may include a pad that senses a magnitude and a distribution of pressures applied by both feet of the user to generate posture information from a pressure signal, the method may further include receiving the pressure signal from the pad, generating the posture information from the received pressure signal, and changing the display image such that the display image corresponds to the posture information, the display image may include at least one of a background image, a letter, a number, a symbol, a graph, and an emoji, which correspond to the heart rate information, and at least one of a background image, a letter, a number, a symbol, a graph, and an emoji, which correspond to the posture information, and the at least one of the background image, the letter, the number, the symbol, the graph, and the emoji, which correspond to the heart rate information, and the at least one of the background image, the letter, the number, the symbol, the graph, and the emoji, which correspond to the posture information may be reproduced at the same time or alternately.

Furthermore, the method may further include classifying the posture of the user into any one of a correct posture, a poor upper body posture, and a posture with crossed legs by using the posture information, the poor upper body posture may include at least one of a first posture, in which an upper body or a neck of the user is bent to any one of an upper side, a lower side, a left side, and a right side, and a second posture, in which a body of the user is leaned or supported by any one of both legs of user, and the at least one of the background image, the letter, the number, the symbol, the graph, and the emoji corresponding to the heart rate information may be differently expressed according to the posture of the user.

Furthermore, the robot may further include a first leg and a second leg driven to correspond to the posture information in the posture with the crossed legs, and a first driver that drives the first leg and the second leg, the first driver may include a first motor, a rack gear that moves to one side and an opposite side by the first motor, a first driven gear disposed in the first leg, and a second driven gear disposed in the second leg, the rack gear may move to the one side to be enmeshed with the first driven gear through forward rotation driving of the first motor to rotate the first driven gear, the rack gear may move to the opposite side to be enmeshed with the second driven gear through reverse rotation driving of the first motor to rotate the second driven gear, and rotary shafts of the first driven gear and the second driven gear may be parallel to each other and rotational directions of the first driven gear and the second driven gear may be opposite to each other.

Furthermore, the case may include an upper case tilted to correspond to the posture information in the poor upper body posture, and a lower case disposed on a lower side of the upper case, and the robot may further include a second driver that tilts the upper case in at least one of a forward/rearward direction and a leftward/rightward direction.

Then, the second driver may include a first bracket, a (2-1)-th motor that rotates the first bracket, a second bracket, and a (2-2)-th motor that rotates the first bracket, one side of the first bracket may be fixed to the upper case, and an opposite side of the first bracket may interwork with a shaft of the (2-1)-th motor and may be hinge-coupled to the second bracket, and one side of the second bracket may be fixed to the upper case, and an opposite side of the second bracket may interwork with a shaft of the (2-2)-th motor.

Furthermore, the first bracket may rotate such that the upper case is tilted forwards, through forward rotation driving of the (2-1)-th motor, the first bracket may rotate such that the upper case is tilted rearwards, through reverse rotation driving of the (2-1)-th motor, the second bracket may rotate such that the upper case is tilted leftwards, through forward rotation driving of the (2-2)-th motor, and the second bracket may rotate such that the upper case is tilted rightwards, through reverse rotation driving of the (2-2)-th motor.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
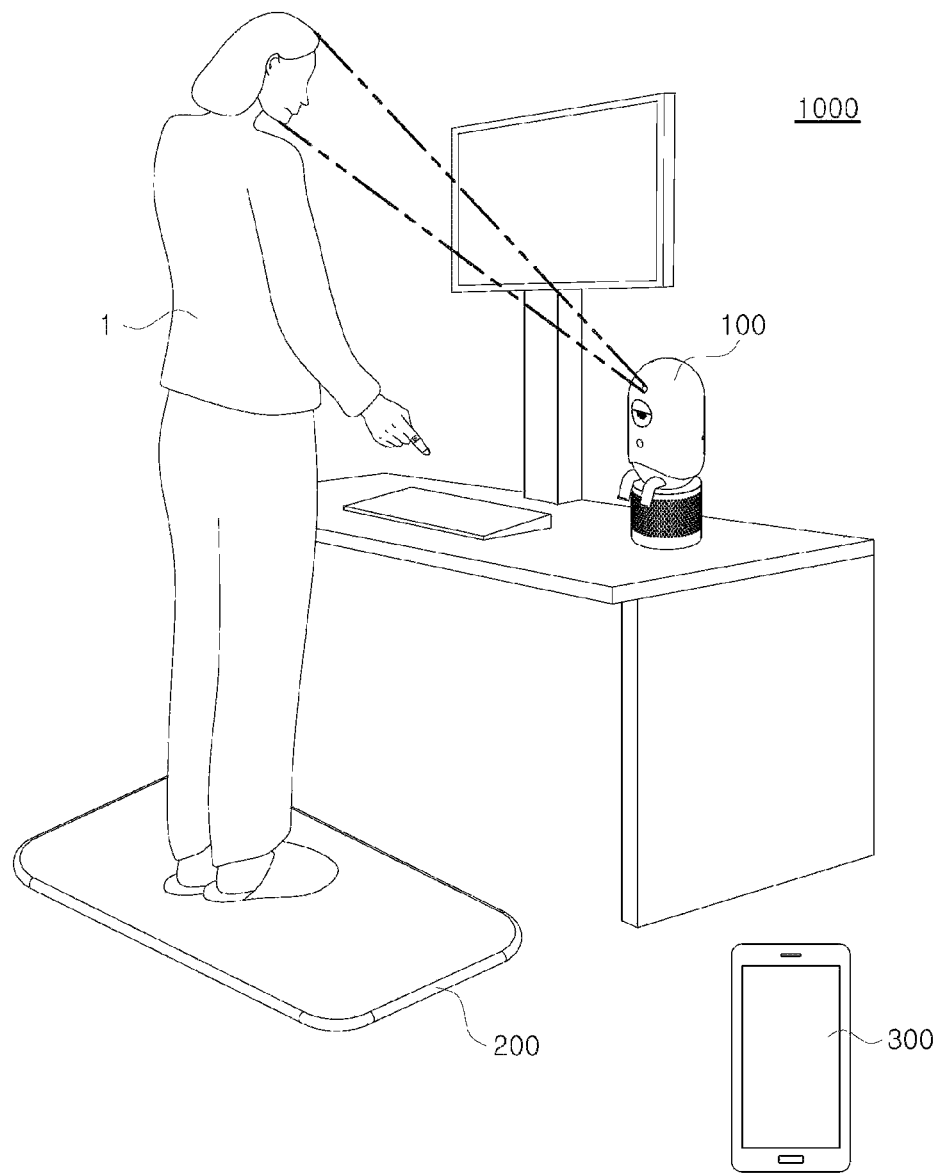
FIG. 1 is a conceptual view illustrating a posture monitoring system according to the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms, such as "below", "beneath", "lower", "above", and "upper", which are spatially relative may be used to easily describe a correlation between one element and other elements as illustrated in the drawings. The spatially relative terms have to be understood as terms including different directions of the elements during use or an operation, in addition to the direction illustrated in the drawings. For example, when the elements illustrated in the drawings are overturned, the elements "below" or "beneath" another element may be positioned "above" the other element. Accordingly, the term "below" or "beneath" may include "below" or "beneath" and "above". The element may be oriented in different directions, and accordingly, the spatially relative terms may be construed according to the orientation.

Hereinafter, a "lengthwise direction" may mean a direction, in which the height of a patient is substantially formed when the patient is laid. Furthermore, a "widthwise direction" may mean a direction, in which both shoulders of the patient are substantially spaced apart from each other when the patient is laid. A "vertical direction" may mean a direction that is substantially perpendicular to both the "lengthwise direction" and the "widthwise direction". The "vertical direction" may be referred to as an "upward/downward direction".

Figure 2:
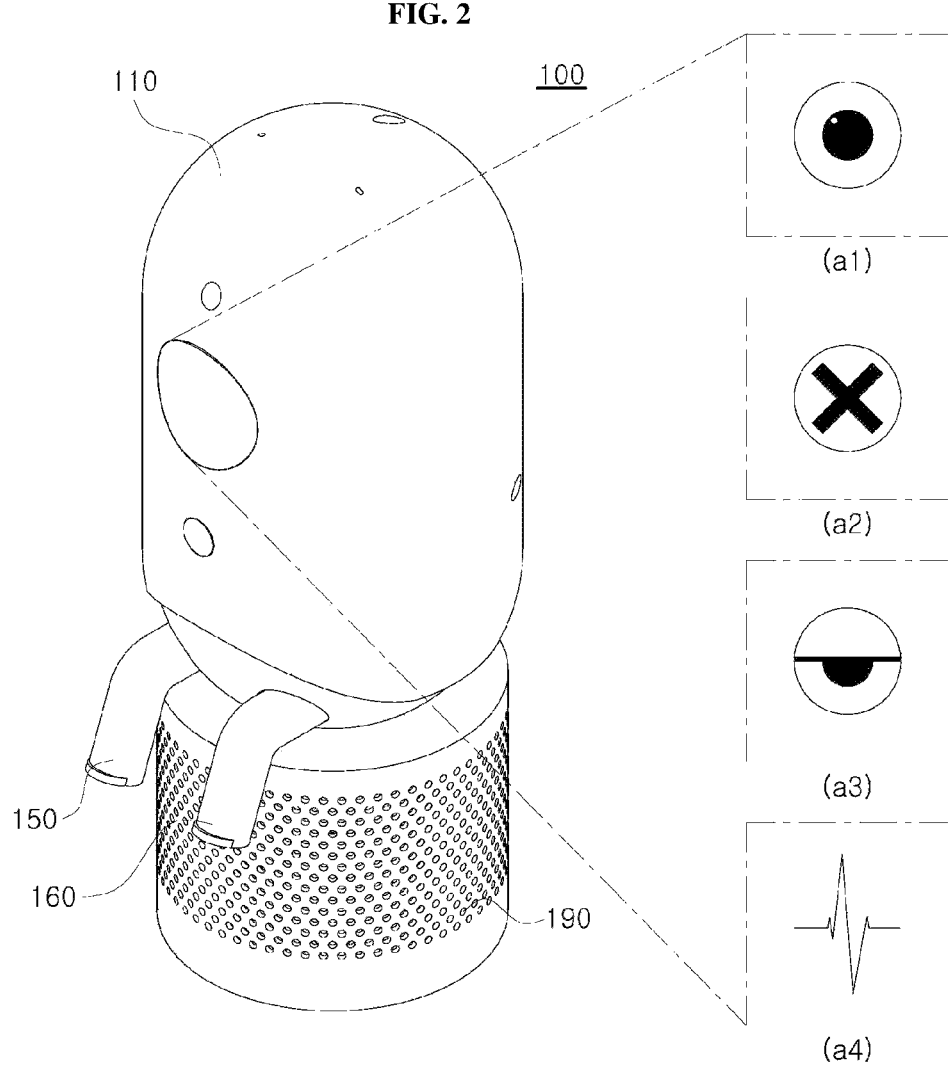
FIG. 2 is a perspective view illustrating a robot according to the inventive concept.
Figure 3:
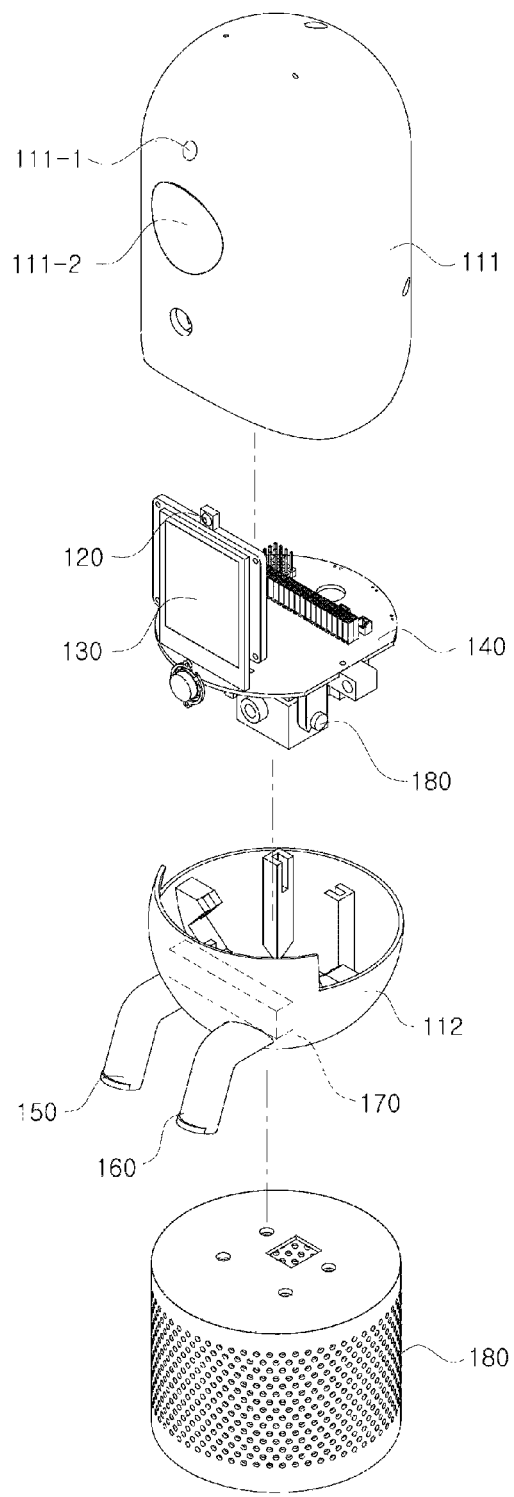
FIG. 3 is an exploded view illustrating a robot according to the inventive concept.
Figure 4:
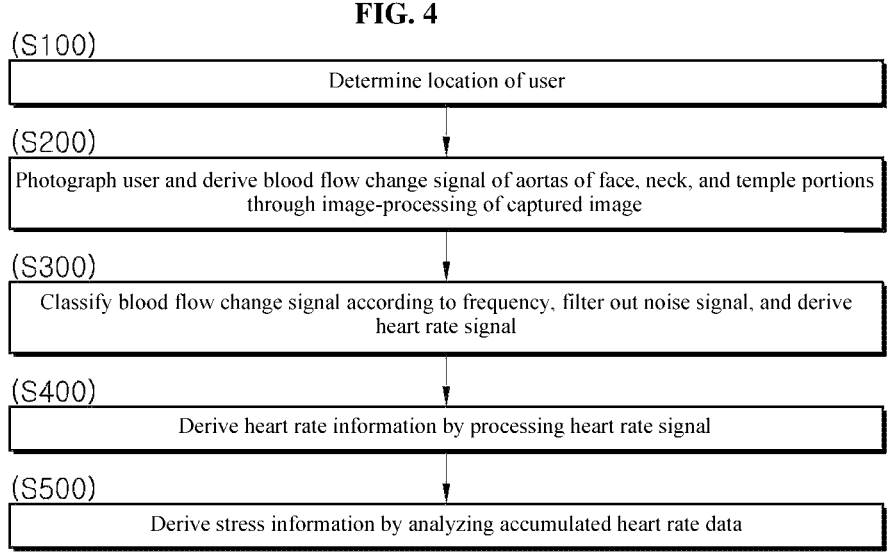
FIG. 4 is a flowchart illustrating a method for deriving heart rate information according to the inventive concept.
Figure 5:
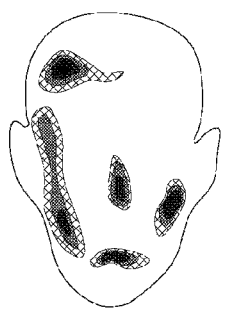
FIG. 5 is a conceptual view illustrating a method for deriving heart rate information according to the inventive concept.
Figure 5:
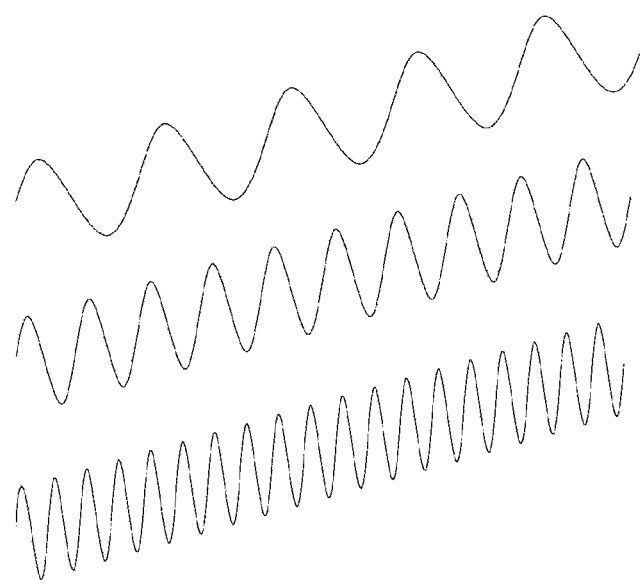
Figure 5:
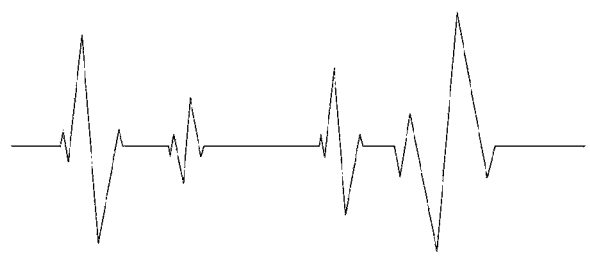
Figure 6:
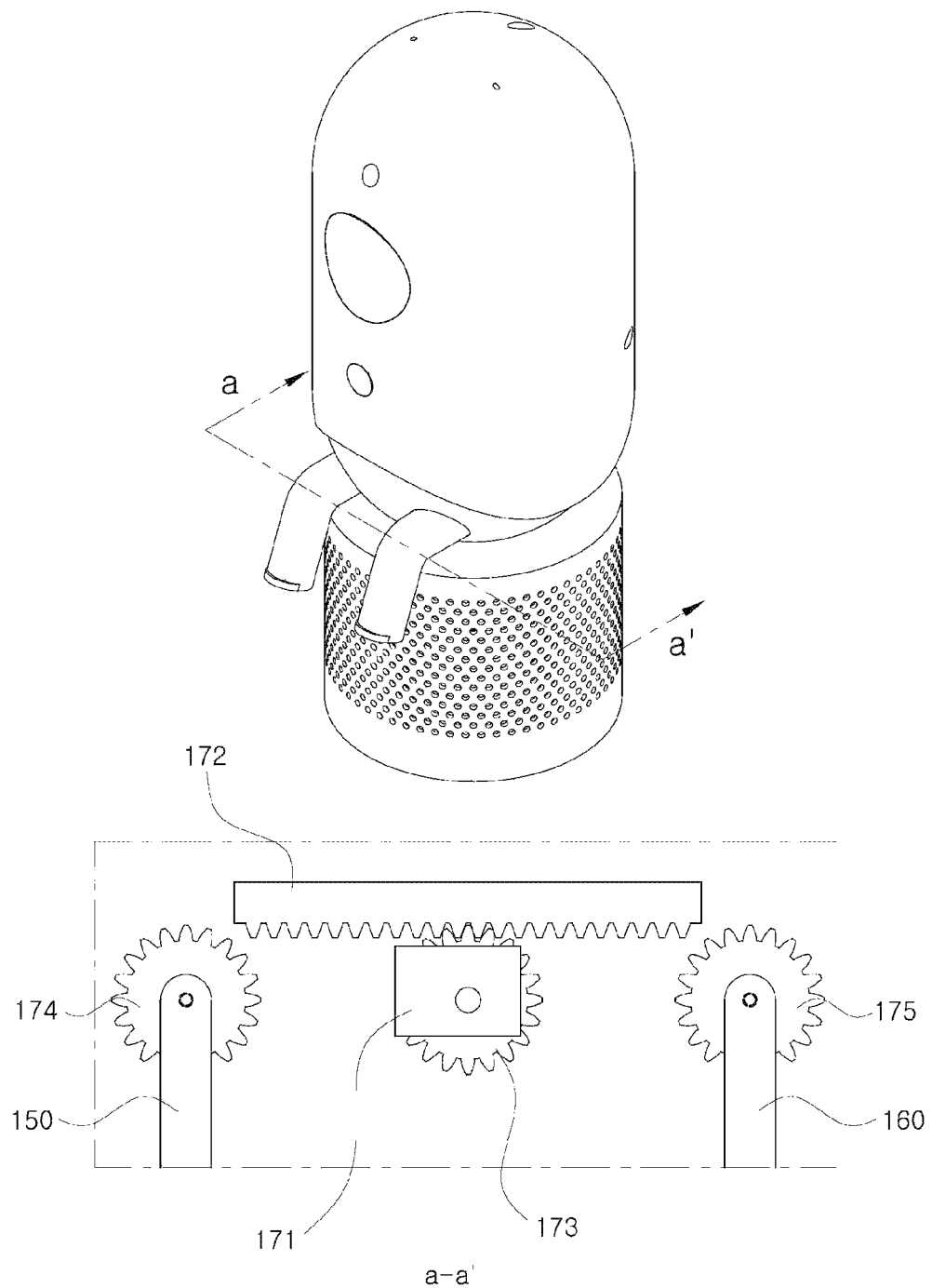
FIGS. 6 to 8 are perspective views and conceptual views illustrating that a first leg and a second leg are driven when a user takes a correct posture and a posture with crossed legs.
Figure 7:
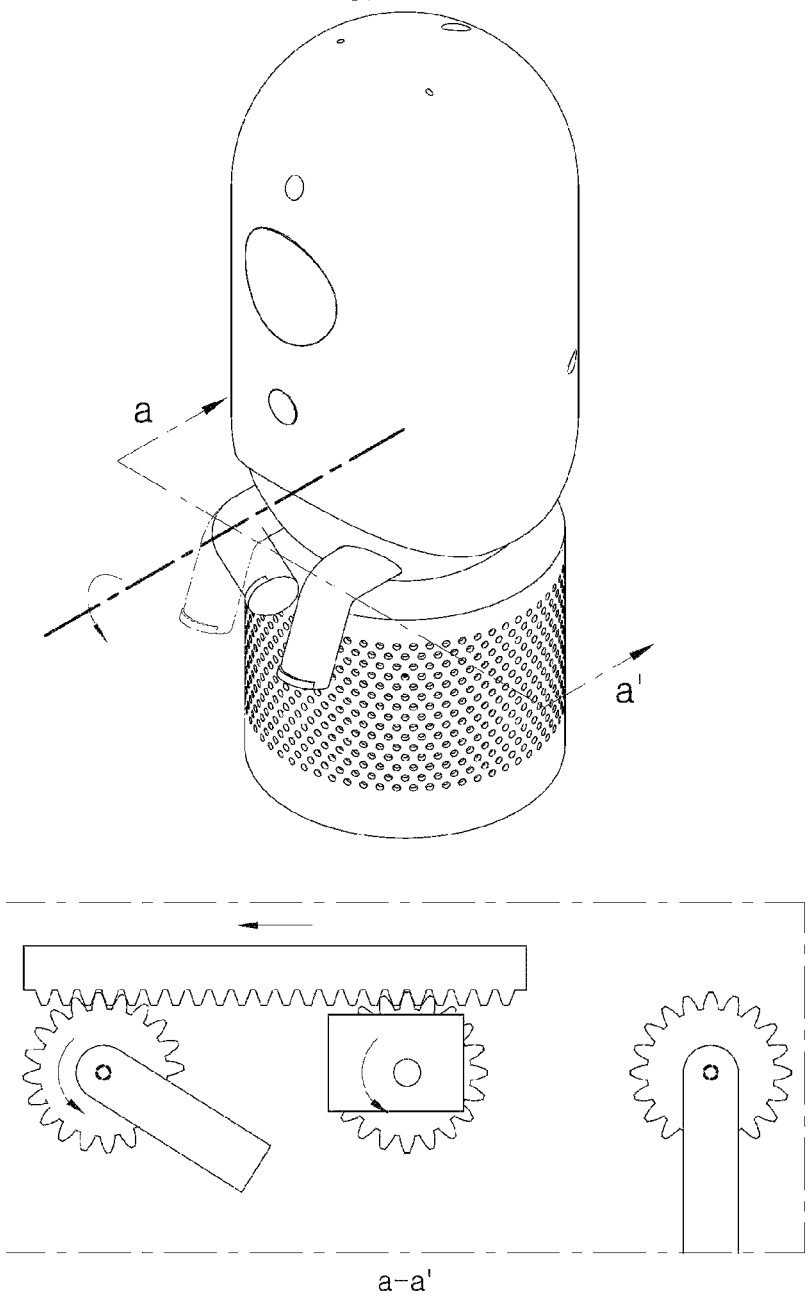
Figure 8:
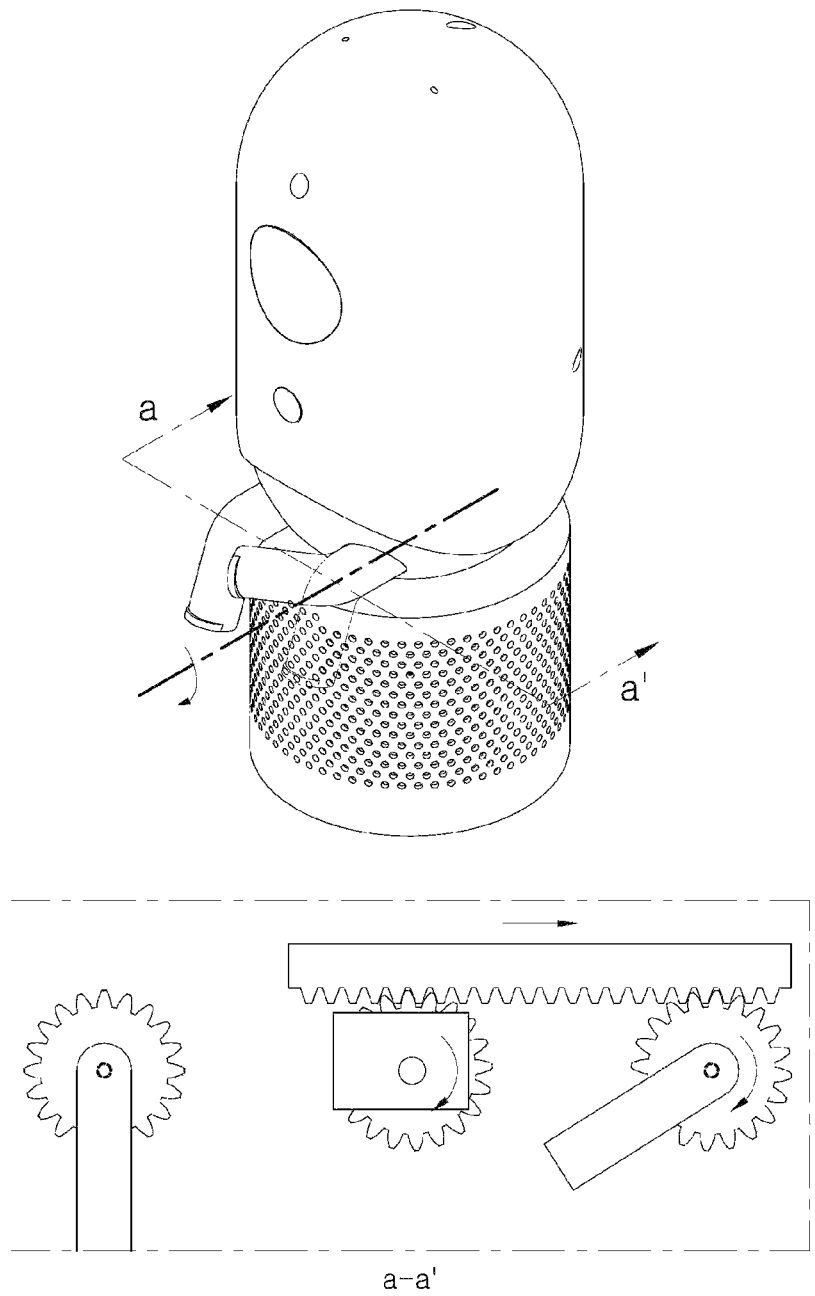
Figure 9:
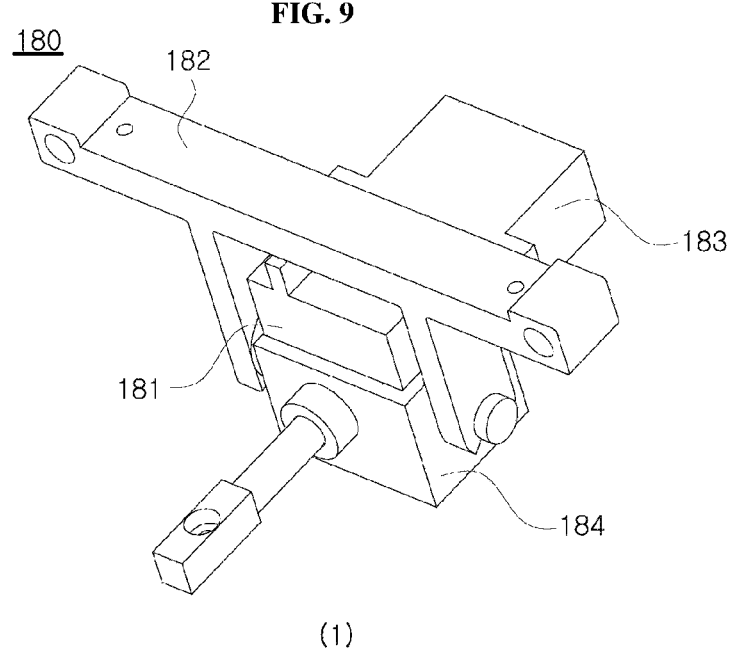
FIG. 9(1) is a perspective view illustrating a second driver of a robot according to the inventive concept, and FIG. 9(2) is a perspective view illustrating the second driver of the robot according to the inventive concept, when viewed from a direction that is opposite to that of FIG. 9(1)
Figure 9:
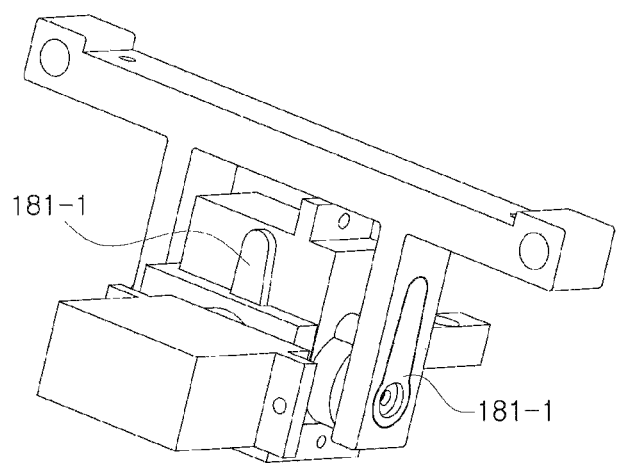
Figure 10:
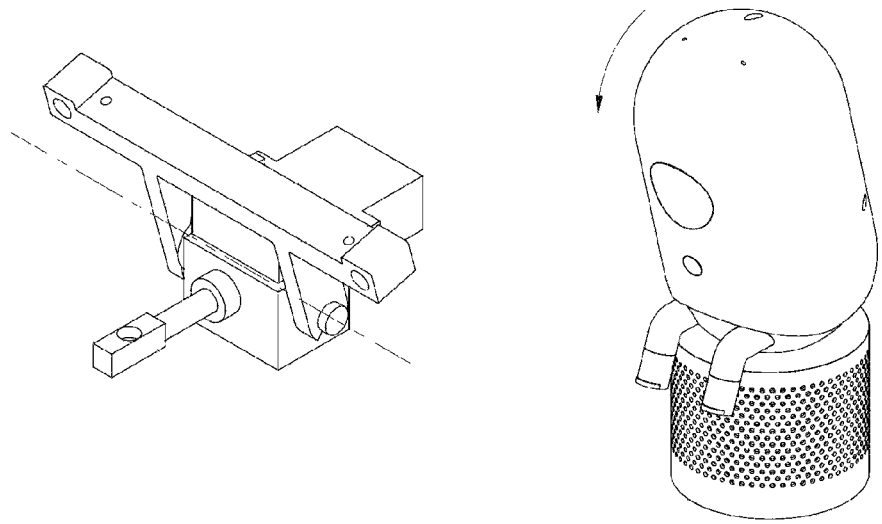
FIGS. 10 and 11 are perspective views illustrating that an upper case of a robot is tilted when a user takes a poor upper body posture.
Figure 10:
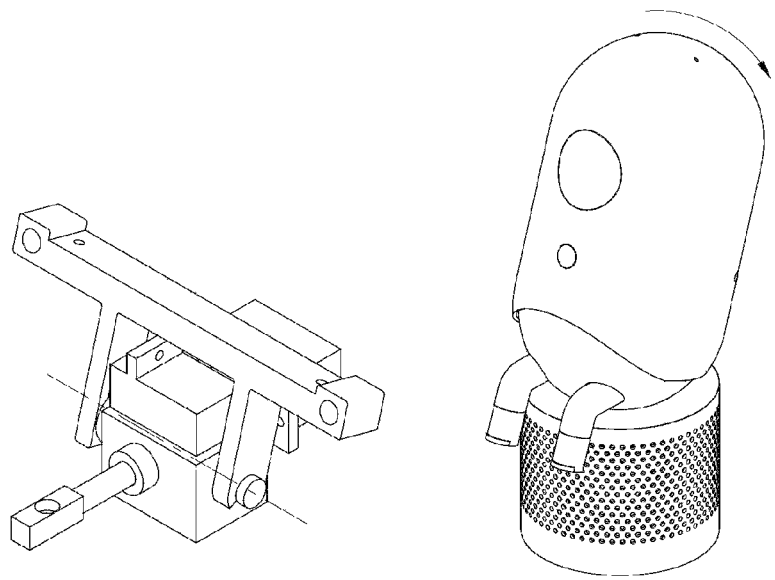
Figure 11:
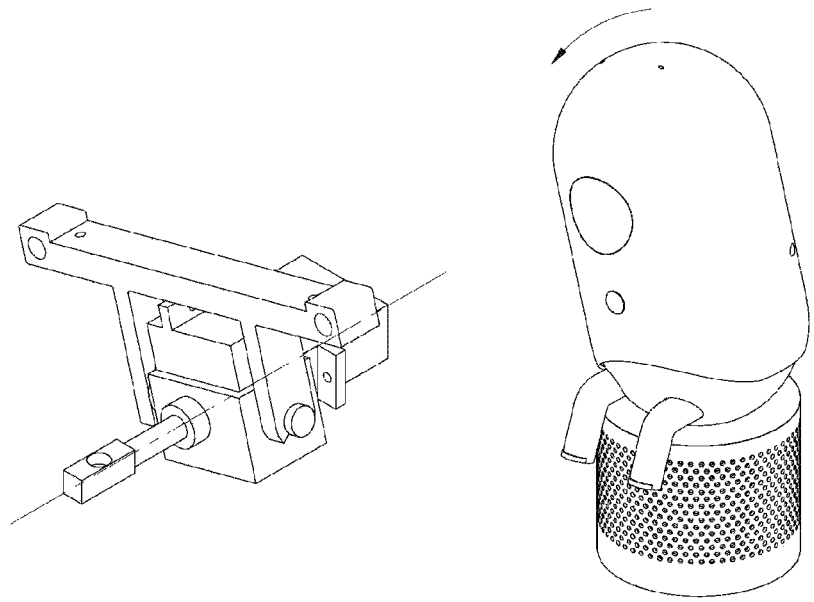
Figure 11:
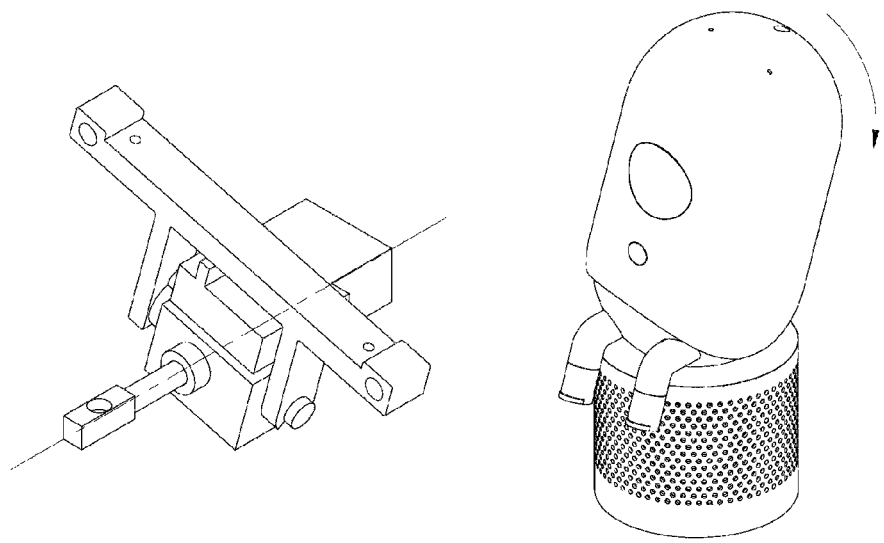

Hereinafter, a posture monitoring system 1000 according to the inventive concept will be described with reference to the drawings. FIG. 1 is a conceptual view illustrating a posture monitoring system according to the inventive concept. FIG. 2 is a perspective view illustrating a robot according to the inventive concept. FIG. 3 is an exploded view illustrating a robot according to the inventive concept. FIG. 4 is a flowchart illustrating a method for deriving heart rate information according to the inventive concept. FIG. 5 is a conceptual view illustrating a method for deriving heart rate information according to the inventive concept. FIGS. 6 to 8 are perspective views and conceptual views illustrating that a first leg and a second leg are driven when a user takes a correct posture and a posture with crossed legs. FIG. 9(1) is a perspective view illustrating a second driver of a robot according to the inventive concept, and FIG. 9(2) is a perspective view illustrating the second driver of the robot according to the inventive concept, when viewed from a direction that is opposite to that of FIG. 9(1). FIGS. 10 and 11 are perspective views illustrating that an upper case of a robot is tilted when a user takes a poor upper body posture.

Hereinafter, although it will be described as an example that a posture monitoring system 1000 according to the inventive concept is provided for a user who performs an operation on a standing disk, the posture monitoring system 1000 according to the inventive concept is not limited to the standing disk. As an example, the posture monitoring system 1000 according to the inventive concept may be provided for a user who performs an operation in various environments, such as a standing disk.

The posture monitoring system 1000 according to the inventive concept may include a robot 100, a pad 200, and a user device 300.

The pad 200 may be seated under both feet of the user, and may sense a magnitude and a distribution of pressures applied to both the feet of the user to derive a pressure signal. To achieve this, a pressure sensor may be embedded in the pad 200. However, the pad 200 according to the inventive concept is not limited thereto. That is, various kinds of sensors that provide a source for determining a posture of the user may be used in the pad 200 according to the inventive concept.

An application (APP) for the posture monitoring system 1000 may be provided in the user device 300. The user device 300 may receive "heart rate information" and "posture information" through communication with the robot 100 and the pad 200, provide an app image list (day records for health) expressed in tables or graphs by converting the information to a database and performing a diagnosis, and provide various coating contents (videos for a method for relieving stresses, correction of posture, and the like) corresponding to the diagnosis result.

To achieve this, one or more of an electric communication device, such as a smartphone, a tablet, a PDA, or a laptop, and a remote controller may be used for the user device 300, the user device 300 according to the inventive concept is not limited thereto.

Hereinafter, the robot 100 according to the inventive concept will be described. The robot 100 may measure the "heart rate information (related to a stress index) of a user 1 and may induce the user 1 to perceive his or her stresses and voluntarily manage the stress by reproducing the measured heart rate information in various "display images".

Further, the robot 100 may receive the pressure signal from the pad 200, and may induce the user 1 to perceive his or her posture and voluntarily take a correct posture by deriving the "posture information" of the user 1 from the received pressure signal and expressing the posture information in various "display images" and through "driving of mimicking of the user".

The robot 100 may include a case 110, a camera 120, a display 130, a board 140, a first leg 150, a second leg 160, a first driver 170, a second driver 180, an artificial intelligence speaker 190, and an electronic control unit (ECU) (not illustrated).

The case 110 may be an external member that forms an external appearance of the robot 100. The case 110 may be manufactured through plastic injection-molding, but the inventive concept is not limited thereto.

The camera 120, the display 130, the board 140, the first driver 170, and the second driver 180 may be disposed in an interior of the case 110. A first window 111-1 for providing an optical path of the camera 120 may be formed in the case 110. Furthermore, a second window 111-2 for exposing the display 130 to the outside may be formed in the case 110.

The first leg 150 and the second leg 160 may be disposed at lower portions of the case 110. The first leg 150 and the second leg 160 may be driven to mimic the posture of the user, and may be exposed to the outside of the case 110 to allow the user to perceive his or her posture.

The artificial intelligence speaker 190 may be disposed on a lower side of the case 110. The case 110 may be supported or held by the artificial intelligence speaker 190.

The case 110 may include an upper case 111 and a lower case 112. An interior space of the case 110 may be formed through coupling of the upper case 111 and the lower case 112.

Meanwhile, the first window 111-1 and the second window 111-2 may be formed in the upper case 111, the first leg 150 and the second leg 160 may be disposed in the lower case 112, and the lower case 112 may be supported by the artificial intelligence speaker 190.

Furthermore, the upper case 111 may be disposed on an upper side of the lower case 112, and may be tilted in at least one of a forward/rear direction and a leftward/rightward direction by the second driver 180 when the user takes a poor upper body posture.

The camera 120 may generate a captured image by photographing the user 1. The captured image of the camera 120 may be utilized to derive the "heart rate information (related to a stress index)". As an example, the electronic control unit may derive a blood flow change signal from the captured image of the camera 120, and may derive the "heart rate information" by processing the derived blood flow change signal.

To achieve this, the camera 120 may be an infrared (IR) camera that acquires light of an infrared wavelength band and generates a captured image, but the inventive concept is not limited thereto.

That is, various kinds of cameras that provide a source for determining the "heart rate information" of the user 1 may be utilized as the camera 120 according to the inventive concept, and moreover, the camera 120 according to the inventive concept may be replaced by various kinds of sensors that show substantially the same functions.

The camera 120 may mainly photograph at least one of a face portion and a neck portion of the user as a subject. This is because the face portion and the neck portion of the user 1 may be easily derived by analyzing changes in vibration and temperatures of aortas.

Meanwhile, the camera 120 may be controlled by the electronic control unit, and may photograph the face portion and the neck portion of the user 1 while focusing on them when it is determined that the user is located in a photographing area.

A "display image" may be reproduced on the display 130. The "display image" may include at least one of a background, a letter, a number, a graph, and an emoji corresponding to the "heart rate information" and/or the "posture information" of the user 1 (see a1, a2, a3, and a4 of FIG. 2).

In this case, the at least one of the background, the letter, the number, the symbol, the graph, and the emoji corresponding to the "heart rate information" of the user 1 and the at least one of the background, the letter, the number, the symbol, the graph, and the emoji corresponding to the "posture information" of the user 1 may be reproduced on the display 130 at the same time or alternately at different times.

That is, the image corresponding to the "heart rate information" of the user 1 and the image corresponding to the "posture information" of the user 1 may be expressed in one frame, and may be expressed in different frames.

However, the inventive concept is not limited thereto, and the "display image" according to the inventive concept may be reproduced in various methods. As an example, only an image corresponding to the "heart rate information" of the user 1 may be reproduced on the display 130, but to the contrary, only an image corresponding to the "posture information" of the user 1 may be reproduced on the display 130.

Meanwhile, various kinds of display panels (an LED, an LCD, and the like) may be used for the display 130. As an example, a thin film transistor liquid crystal display (TFT LCD) may be used as the display 130 according to the inventive concept.

The board 140 may be a printed circuit board (PCB). Various electronic components may be mounted on the board 140. As an example, the camera 120 and the display 130 may be mounted on the board 140, and the electronic control unit may be mounted on the board 140. Accordingly, the camera 120 and the display 130 may transmit and receive signals to and from the electronic control unit, and may receive a control signal from the electronic control unit.

The first leg 150 and the second leg 160 are members corresponding to both the legs of the user 1, and may be driven to mimic the user 1 in a posture with the crossed legs of the user 1.

The first driver 170 may be a member that rotates the first leg 150 and the second leg 160, and the second driver 180 may a member that tilts the upper case 111.

The artificial intelligence speaker 190 is configured to provide information that is useful for an operation of the user 1, and may understand the question of the user 1 through natural language processing (NLP), neutral machine translation (NMT), and the like and provide an answer that is matched with a question of the user 1 by using AI-based big data (provision of a chatter robot service).

The electronic control unit (not illustrated) may communicate with the camera 120, the display 130, the driver 170, and the pad 200, and may receive the captured image from the camera 120 and receive the pressure signal from the pad 200 to generate the "heart rate information" and the "posture information". Moreover, the electronic control unit may control the display 130 and the first driver 170 according to the "heart rate information" and the "posture information".

The electronic control unit may be embedded in the robot 100 and be embedded in the user device 300, and may be divided and be embedded in the robot 100 and the user device 300, respectively.

When the electronic control unit is embedded in the user device 300, the user device 300 may perform the function of providing the above-described app image list or providing the coaching contents and the functions performed by the electronic control unit as well in substantially the same way.

Hereinafter, it will be described that the robot 100 according to the inventive concept expresses a state of the user 1 in a "display image" by using the "heart rate information".

As illustrated in FIG. 4, a method for deriving a "heart rate information" from a captured image may include an operation S100 of determining a location of the user 1, an operation S200 of deriving a blood flow change signal through image-processing of the captured image, an operation S300 of deriving a heart rate signal from the blood flow change signal, and an operation S400 of deriving "heart rate information" by processing the heart rate signal.

In the operation S100 of determining the location of the user 1, the electronic control unit may analyze the captured image of the camera 120 or may determine whether the user 1 is located in a photographing area by using a sensing signal of a location detection sensor (to achieve this, the robot or the posture monitoring system according to the inventive concept may further include a location detection sensor as an element).

The operation S200 of deriving the blood flow change signal through the image-processing of the captured image may be performed after it is identified that the user 1 is located in the photographing area.

When the user 1 is located in the photographing area, the electronic control unit may determine the locations of the face portion and the neck portion of the user 1 by utilizing an image, location information, or 3-dimensional depth data, and may drive the camera 120 such that the photographing area of the camera 120 faces the face portion and the neck portion of the user 1. To achieve this, the robot 100 according to the inventive concept may further include a "camera driving device".

The electronic control unit may derive a blood flow change signal of at least one of the face portion (particularly, a temple portion) and the neck portion of the user. In this case, the blood flow change signal, as illustrated in FIG. 5(1), may be a signal obtained by deriving at least one of a vibration value and a temperature change value of aortas of at least one of the face portion and the neck portion of the user by analyzing a thermal image that is captured in real time. That is, the blood flow change signal may be a signal on the at least one of the vibration value and the temperature change value of the aortas of the at least one of the face portion and the neck portion of the user 1.

Next, the electronic control unit may classify the blood flow change signal of the user 1 according to its frequency, and may derive a heart rate signal by filtering out a noise signal. That is, the blood flow change signal, as illustrated in FIG. 5(2), may include a signal that is not related to heart rates. The electronic control unit may extract only the heart rate signal through a process of classifying the blood flow change signal according to its frequency through a fast Fourier transform (FFT) and removing the noise signal, other than the heart rate signal, through a digital band pass filter (DBPF).

Next, the electronic control unit may derive the heart rate information from the heart rate signal by using a maximum extraction algorithm. As a result, as illustrated in FIG. 5(3), the "heart rate information" may be derived.

The electronic control unit may change the display image such that the display image includes at least one of a background, a letter, a number (value), a symbol, a graph, and an emoji corresponding to the "heart rate information" As an example, as illustrated in FIG. 2(a4), a heart rate graph may be reproduced on the display 130.

Meanwhile, because the "heart rate information" is renewed in real time, the image corresponding to the "heart rate information" may be changed in real time. That is, because the "heart rate information" is expressed on the display 130 as the image that is changed in real time, the user 1 may monitor his or her state (stress state) in real time.

The electronic control unit may classify the state of the user 1 into a normal heart rate state, a low heart rate state, and a high heart rate state, by using the "heart rate information". In this case, the at least one of the background, the letter, the number, the symbol, the graph, and the emoji corresponding to the "heart rate information" may be expressed differently according to the states of the user 1. Accordingly, the user 1 may intuitively recognize the normal heart rate state, the low heart rate state, and the high heart rate state.

As an example, because the heart rate fluctuates with a high width when the user 1 receives many stresses, images corresponding to the low heart rate state and the high heart rate state mainly appear on the display 130. In this case, the user 1 may take an appropriate rest by recognizing the stresses by himself or herself, through monitoring of the display image.

To the contrary, because the heart rates show a stable aspect when the user 1 hardly receives stresses, images corresponding to the normal heart rate state mainly appear on the display 130. In this case, the user 1 may recognize by himself or herself that he or she is in a normal state, through monitoring of the display image.

Hereinafter, it will be described that the robot 100 according to the inventive concept expresses a posture of the user 1 in a "display image" and through "driving of mimicking of the user", by using "posture information".

A magnitude and a distribution of pressures applied to both feet of the user may be sensed by the pad 200 and may be derived as a pressure signal. The electronic control unit may derive "posture information" on the posture of the user 1 by processing the pressure signal. Meanwhile, various technologies for allowing an ordinary person to easily perform the method for deriving "posture information" from the pressure signal may be used.

The electronic control unit may change the display image such that the display image includes at least one of a background, a letter, a number (value), a symbol, a graph, and an emoji corresponding to the "posture information".

Meanwhile, because the "posture information" is renewed in real time, the image corresponding to the "posture information" may be changed in real time. That is, because the "posture information" is expressed on the display 130 as an image that is changed in real time, the user 1 may monitor his or her posture in real time.

The electronic control unit may classify the postures of the user 1 into a correct posture, a poor upper body posture, and a posture with the crossed legs, by using the "posture information". In this case, the at least one of the background, the letter, the number, the symbol, the graph, and the emoji corresponding to the "posture information" may be expressed differently according to the postures of the user 1.

Meanwhile, the poor upper body posture may include at least one of a first posture, in which the upper body or the neck is bent to any one of the upper side, the lower side, the left side, and the right side, and a second posture, in which the body is leaned or supported by any one of both the legs, or may be a combination form of the first and second postures.

As an example, the emoji as in FIG. 2(a1) may be reproduced in the correct posture on the display 130, the emoji as in FIG. 2(a2) may be reproduced in the poor upper body posture, and the emoji as in FIG. 2(a3) may be reproduced in the posture with the crossed legs. Accordingly, the user 1 may intuitively recognize his or her posture.

Moreover, the electronic control unit may classify the correct posture, the poor upper body posture, and the posture with the crossed legs more finely, by using the "posture information", and the image corresponding to the "posture information" may be expressed differently according to the case.

Meanwhile, as described above, the electronic control unit may reproduce the image corresponding to the "heart rate information" and the image corresponding to the "posture information" at the same time, or may reproduce the images at different times. Moreover, the electronic control unit may perform a control to reproduce the image corresponding to the "heart rate information" and the image corresponding to the "posture information" alternately.

The electronic control unit may control the first driver 170 such that the first leg 150 and the second leg 160 rotate in correspondence to the "posture information", when the user 1 takes the posture with the crossed legs. In this case, the first leg 150 and the second leg 160 allow the user 1 to perceive the posture with the crossed legs by mimicking the posture with the crossed legs of the user 1.

As illustrated in FIG. 6, when the user 1 is in the correct posture (likewise in the case of the poor upper body posture), the first driver 170 does not perform a driving operation and the first leg 150 and the second leg 160 may be fixed in an original state. In this case, the first leg 150 and the second leg 160 may be disposed in parallel to each other, and may mimic the correct posture of the user 1.

As illustrated in FIG. 7, when the user 1 is in a posture with the right leg crossed, the first leg 150 may rotate by the first driver 170. In this case, the rotational direction of the first leg 150 is a counterclockwise direction and the rotational radius of the first leg 150 is about 90 degrees when the first leg 150 is viewed from the front side, and thus the posture with the right leg crossed of the user may be mimicked.

As illustrated in FIG. 8, when the user 1 is in a posture with the left leg crossed, the second leg 160 may rotate by the first driver 170. In this case, the rotational direction of the second leg 160 is a clockwise direction and the rotational radius of the second leg 160 is about 90 degrees when the second leg 160 is viewed from the front side, and thus the posture with the left leg crossed of the user 1 may be mimicked.

Meanwhile, the robot 100 according to the inventive concept may drive the first leg 150 and the second leg 160 with one motor to lower production costs and thus secure a price competitiveness.

To achieve this, the first driver 170 may include a first motor 171, a rack gear 172, a driving gear 173, a first driven gear 174, and a second driven gear 175.

The driving gear 173 is a gear that is driven by the first motor 171, and may be disposed in a shaft of the first motor 171. The rack gear 172 may be always enmeshed with the driving gear 173, and may move to one side and an opposite side through forward rotation and reverse rotation of the first motor 171.

The first driven gear 174 may be disposed in the first leg 150, and may be selectively enmeshed with the rack gear 172 to rotate as the rack gear 172 moves to one side (to the right side). That is, the first driven gear 174 may be enmeshed with the rack gear 172 to rotate when the rack gear 172 moves to the one side through forward rotation of the first motor 171.

The second driven gear 175 may be disposed in the second leg 160, and may be selectively enmeshed with the rack gear 172 to rotate as the rack gear 172 moves to an opposite side (to the left side). That is, the second driven gear 175 may be enmeshed with the rack gear 172 to rotate when the rack gear 172 moves to the opposite side through reverse rotation of the first motor 171.

Meanwhile, the axes of rotation of the first driven gear 174 and the second driven gear 175 may be parallel to each other, and the rotational directions thereof may be opposite to each other. Accordingly, the first leg 150 and the second leg 160 rotate in opposite directions while being disposed to be parallel to each other to implement the posture with the crossed legs.

The electronic control unit may control the second driver 180 such that the upper case 111 is tilted in correspondence to the "posture information" when the user 1 takes the poor upper body posture. In this case, the upper case 111 may mimic the poor upper body posture of the user 1 (the upper case is tilted in a direction in which the upper body of the user is inclined) so that the user 1 may perceive the poor upper body posture.

Meanwhile, the second driver 180 may tilt the upper case 111 to the front side and the rear side (in the forward/rearward direction) so that the case, in which the upper body of the user 1 is inclined to the front side, and the case, in which the upper body of the user 1 is inclined to the rear side, may be mimicked. Further, the second driver 180 according to the inventive concept may tilt the upper case 111 to the left side and the right side (in the leftward/rightward direction) so that the case, in which the upper body of the user 1 is inclined to the left side, and the case, in which the upper body of the user 1 is inclined to the right side, may be mimicked.

To achieve this, the second driver 180 may include a (2-1)-th motor 181, a first bracket 182, a (2-2)-th motor 183, and a second bracket 184. The (2-1)-th motor 181 may rotate the first bracket 182, the (2-2)-th motor 183 may rotate the second bracket 184, and the upper case 111 may be supported by the first bracket 182 and the second bracket 184 to be tilted in the forward/rearward direction and the leftward/rightward direction.

To achieve this, one side (an upper bar) of the first bracket 182 may be fixed to the upper case 111, and an opposite side (a pair of links extending from a horizontal bar to the lower side) of the first bracket 182 may interwork (one-side link) with a shaft of the (2-1)-th motor 181 and be hinge-coupled (another-side link) to the second bracket 184 as well.

Furthermore, one side (a front portion) of the second bracket 184 may be fixed to the upper case 111, and an opposite side (a rear portion) of the second bracket 184 may interwork with a shaft of the (2-2)-th motor 183.

Meanwhile, the (2-1)-th motor 181 may be disposed substantially between the one side (the upper bar) of the first bracket 182 and the second bracket 184, and accordingly, the second driver 180 according to the inventive concept may have a compact structure.

Moreover, the shaft of the (2-1)-th motor 181 and the opposite side of the first bracket 182, and the shaft of the (2-2)-th motor 183 and the opposite side of the second bracket 184 may interwork with each other through a cam 181-1 to stably implement rotation thereof.

As illustrated in FIG. 10(1), when the user 1 takes a posture, in which the upper body is inclined to the front side, the first bracket 182 may rotate such that the upper case 111 is tilted to the front side through forward rotation of the (2-1)-th motor 181 to mimic the posture of the user 1, in which the upper body is inclined to the front side. In this case, the rotational radius of the first bracket 182 may be about less than 90 degrees (an acute angle).

As illustrated in FIG. 10(2), when the user 1 takes a posture, in which the upper body is inclined to the rear side, the first bracket 182 may rotate such that the upper case 111 is tilted to the rear side through reverse rotation of the (2-1)-th motor 181 to mimic the posture of the user 1, in which the upper body is inclined to the rear side. In this case, the rotational radius of the first bracket 182 may be about less than 90 degrees (an acute angle).

As illustrated in FIG. 11(1), when the user 1 takes a posture, in which the upper body is inclined to the left side, the second bracket 184 may rotate such that the upper case 111 is tilted to the left side through forward rotation of the (2-2)-th motor 183 to mimic the posture of the user 1, in which the upper body is inclined to the left side. In this case, the rotational radius of the second bracket 184 may be about less than 90 degrees (an acute angle).

As illustrated in FIG. 11(2), when the user 1 takes a posture, in which the upper body is inclined to the right side, the second bracket 184 may rotate such that the upper case 111 is tilted to the right side through reverse rotation of the (2-2)-th motor 183 to mimic the posture of the user 1, in which the upper body is inclined to the right side. In this case, the rotational radius of the second bracket 184 may be about less than 90 degrees (an acute angle).

The inventive concept provides a robot that photographs a user with a camera, generates heart rate information to analyze a state of the user, and receives a sensing signal from a pad that measures a pressure applied to both feet of the user and generate posture information to analyze a posture of the user.

The robot according to the inventive concept may analyze a state and a posture of a user and express the state and the posture with various kinds of letters, numbers (values), symbols, and emojis corresponding to the state and the posture on a display, thereby allowing the user to monitor the state and the posture of the user in real time.

Furthermore, because the robot according to the inventive concept mimics the posture of the user and rotates its legs when the user crosses his or her legs, the user may perceive that he or she crosses his or her legs.

Furthermore, because the robot according to the inventive concept mimics the posture of the user and tilts the upper case when the upper body of the user is in a poor posture, the user may perceive that his or her upper body is in the poor posture.

Furthermore, the robot according to the inventive concept rotates his or her legs by using one motor of the first driver, costs for a driving module may be decreased and product costs are economical.

In addition, in the robot according to the inventive concept, because a driving member that tilts the upper case is disposed in the second driver, the size of the product may be reduced.

Moreover, in the posture monitoring system according to the inventive concept, because a user device that receives a state and a posture of a user from a robot and provides various stress relief and posture correction contents matched with the state and the posture, the user may receive a coach for management of health and the posture of the user.

The effects of the inventive concept are not limited thereto, and other unmentioned effects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A robot for mimicking a posture of a user, the robot comprising:
   a case;
   a camera disposed in the case, and configured to photograph the user and generate a captured image;
   a display disposed in the case and configured to reproduce a display image;
   an electronic control unit configured to communicate with the camera and the display,
   wherein the electronic control unit derives heart rate information from the captured image, and changes the display image such that the display image corresponds to the heart rate information,
   wherein the electronic control unit communicates with a pad that senses a magnitude and a distribution of pressures applied by both feet of the user to generate posture information from a pressure signal, and changes the display image such that the display image corresponds to the posture information,
   wherein the display image includes at least one of a background image, a letter, a number, a symbol, a graph, and an emoji, which correspond to the heart rate information, and at least one of a background image, a letter, a number, a symbol, a graph, and an emoji, which correspond to the posture information,
   wherein the at least one of the background image, the letter, the number, the symbol, the graph, and the emoji, which correspond to the heart rate information, and the at least one of the background image, the letter, the number, the symbol, the graph, and the emoji, which correspond to the posture information are reproduced at the same time or alternately, wherein the electronic control unit classifies the posture of the user into any one of a correct posture, a poor upper body posture, and a posture with crossed legs, wherein the poor upper body posture includes at least one of a first posture, in which an upper body or a neck of the user is bent to any one of an upper side, a lower side, a left side, and a right side, and a second posture, in which a body of the user is leaned or supported by any one of both legs of user, and wherein the at least one of the background image, the letter, the number, the symbol, the graph, and the emoji corresponding to the posture information is differently expressed according to the posture of the user;

a first leg and a second leg driven to correspond to the posture information in the posture with the crossed legs, and a first driver configured to drive the first leg and the second leg, wherein the first driver includes:

a first motor;

a rack gear configured to move to one side and an opposite side by the first motor;

a first driven gear disposed in the first leg; and a second driven gear disposed in the second leg, wherein the rack gear moves to the one side to be enmeshed with the first driven gear through forward rotation driving of the first motor to rotate the first driven gear, wherein the rack gear moves to the opposite side to be enmeshed with the second driven gear through reverse rotation driving of the first motor to rotate the second driven gear, and wherein axes of rotation of the first driven gear and the second driven gear are parallel to each other and rotational directions of the first driven gear and the second driven gear are opposite to each other.

2. The robot of claim 1, wherein the camera acquires light of an infrared ray wavelength band and generates the captured image, and wherein the electronic control unit derives a blood flow change signal of at least one of a face portion and a neck portion of the user from the captured image, derives a heart rate signal by classifying the blood flow change signal according to a frequency thereof and filtering out a noise signal, and derives the heart rate information from the heart rate signal by using a maximum point extraction algorithm.

3. The robot of claim 1, wherein the display image includes at least one of a background image, a letter, a number, a symbol, a graph, and an emoji corresponding to the heart rate information, wherein the electronic control unit classifies a state of the user into any one of a normal heart rate state, a low heart rate state, and a high heart rate state, by using the heart rate information, and wherein the at least one of the background image, the letter, the number, the symbol, the graph, and the emoji corresponding to the heart rate information is differently expressed according to the state of the user.

4. The robot of claim 1, wherein the case includes:

an upper case tilted to correspond to the posture information in the poor upper body posture, and a lower case disposed on a lower side of the upper case, and wherein the robot further includes:

a second driver configured to tilt the upper case in at least one of a forward/rearward direction and a leftward/rightward direction.

5. A posture monitoring system comprising the robot of claim 1.

6. A robot for mimicking a posture of a user, the robot comprising:

a case;

a camera disposed in the case, and configured to photograph the user and generate a captured image;

a display disposed in the case and configured to reproduce a display image; and an electronic control unit configured to communicate with the camera and the display, wherein the electronic control unit derives heart rate information from the captured image, and changes the display image such that the display image corresponds to the heart rate information, wherein the electronic control unit communicates with a pad that senses a magnitude and a distribution of pressures applied by both feet of the user to generate posture information from a pressure signal, and changes the display image such that the display image corresponds to the posture information, wherein the display image includes at least one of a background image, a letter, a number, a symbol, a graph, and an emoji, which correspond to the heart rate information, and at least one of a background image, a letter, a number, a symbol, a graph, and an emoji, which correspond to the posture information, wherein the at least one of the background image, the letter, the number, the symbol, the graph, and the emoji, which correspond to the heart rate information, and the at least one of the background image, the letter, the number, the symbol, the graph, and the emoji, which correspond to the posture information are reproduced at the same time or alternately, wherein the electronic control unit classifies the posture of the user into any one of a correct posture, a poor upper body posture, and a posture with crossed legs, wherein the poor upper body posture includes at least one of a first posture, in which an upper body or a neck of the user is bent to any one of an upper side, a lower side, a left side, and a right side, and a second posture, in which a body of the user is leaned or supported by any one of both legs of user, wherein the at least one of the background image, the letter, the number, the symbol, the graph, and the emoji corresponding to the posture information is differently expressed according to the posture of the user, wherein the case includes:

an upper case tilted to correspond to the posture information in the poor upper body posture. and a lower case disposed on a lower side of the upper case, wherein the robot further includes:

a second driver configured to tilt the upper case in at least one of a forward/rearward direction and a leftward/rightward direction, wherein the second driver includes:

a first bracket;

a (2-1)-th motor configured to rotate the first bracket;

a second bracket; and a (2-2)-th motor configured to rotate the first bracket, wherein one side of the first bracket is fixed to the upper case, and an opposite side of the first bracket interworks with a shaft of the (2-1)-th motor and is hinge-coupled to the second bracket, and wherein one side of the second bracket is fixed to the upper case, and an opposite side of the second bracket interworks with a shaft of the (2-2)-th motor.

7. The robot of claim 6, wherein the first bracket rotates such that the upper case is tilted forwards, through forward rotation driving of the (2-1)-th motor,
wherein the first bracket rotates such that the upper case is tilted rearwards, through reverse rotation driving of the (2-1)-th motor,
wherein the second bracket rotates such that the upper case is tilted leftwards, through forward rotation driving of the (2-2)-th motor, and
wherein the second bracket rotates such that the upper case is tilted rightwards, through reverse rotation driving of the (2-2)-th motor.

8. A method for monitoring a posture of a user by using a robot, the method comprising:
generating an image captured by photographing a user, through a camera disposed in a case of the robot;
reproducing a display image, on a display disposed in the case;
deriving heart rate information from the captured image;
changing the display image such that the display image corresponds to the heart rate information,
wherein the robot includes a pad that senses a magnitude and a distribution of pressures applied by both feet of the user to generate posture information from a pressure signal,
wherein the method is further comprising the steps of:
receiving the pressure signal from the pad;
generating posture information from the received pressure signal; and
changing the display image such that the display image corresponds to the posture information,
wherein the display image includes at least one of a background image, a letter, a number, a symbol, a graph, and an emoji, which correspond to the heart rate information, and at least one of a background image, a letter, a number, a symbol, a graph, and an emoji, which correspond to the posture information, and
wherein the at least one of the background image, the letter, the number, the symbol, the graph, and the emoji, which correspond to the heart rate information, and the at least one of the background image, the letter, the number, the symbol, the graph, and the emoji, which correspond to the posture information are reproduced at the same time or alternately; and
classifying the posture of the user into any one of a correct posture, a poor upper body posture, and a posture with crossed legs by using the posture information,
wherein the poor upper body posture includes at least one of a first posture, in which an upper body or a neck of the user is bent to any one of an upper side, a lower side, a left side, and a right side, and a second posture, in which a body of the user is leaned or supported by any one of both legs of user, and
wherein the at least one of the background image, the letter, the number, the symbol, the graph, and the emoji corresponding to the posture information is differently expressed according to the posture of the user,
wherein the robot further includes:
a first leg and a second leg driven to correspond to the posture information in the posture with the crossed legs, and
a first driver configured to drive the first leg and the second leg,
wherein the first driver includes:

a first motor;
a rack gear configured to move to one side and an opposite side by the first motor;
a first driven gear disposed in the first leg; and
a second driven gear disposed in the second leg,
wherein the rack gear moves to the one side to be enmeshed with the first driven gear through forward rotation driving of the first motor to rotate the first driven gear,
wherein the rack gear moves to the opposite side to be enmeshed with the second driven gear through reverse rotation driving of the first motor to rotate the second driven gear, and
wherein rotary shafts of the first driven gear and the second driven gear are parallel to each other and rotational directions of the first driven gear and the second driven gear are opposite to each other.

9. The method of claim 8, wherein the camera acquires light of an infrared ray wavelength band and generates the captured image, and
wherein the deriving of the heart rate information includes:
deriving a blood flow change signal of at least one of a face portion and a neck portion of the user, from the captured image;
deriving a heart rate signal by classifying the blood flow change signal according to a frequency thereof and filtering out a noise signal; and
deriving the heart rate information from the heart rate signal by using a maximum point extraction algorithm.

10. The method of claim 8, wherein the display image includes at least one of a background image, a letter, a number, a symbol, a graph, and an emoji corresponding to the heart rate information,
wherein a state of the user is classified into any one of a normal heart rate state, a low heart rate state, and a high heart rate state, based on the heart rate information, and
wherein the at least one of the background image, the letter, the number, the symbol, the graph, and the emoji corresponding to the heart rate information is differently expressed according to the state of the user.

11. The method of claim 8, wherein the case includes:
an upper case tilted to correspond to the posture information in the poor upper body posture, and
a lower case disposed on a lower side of the upper case, and
wherein the robot further includes:
a second driver configured to tilt the upper case in at least one of a forward/rearward direction and a leftward/rightward direction.

12. The method of claim 11, wherein the second driver includes:
a first bracket;
a (2-1)-th motor configured to rotate the first bracket;
a second bracket; and
a (2-2)-th motor configured to rotate the first bracket,
wherein one side of the first bracket is fixed to the upper case, and an opposite side of the first bracket interworks with a shaft of the (2-1)-th motor and is hinge-coupled to the second bracket, and
wherein one side of the second bracket is fixed to the upper case, and an opposite side of the second bracket interworks with a shaft of the (2-2)-th motor.

13. The method of claim 12, wherein the first bracket rotates such that the upper case is tilted forwards, through forward rotation driving of the (2-1)-th motor, wherein the first bracket rotates such that the upper case is tilted rearwards, through reverse rotation driving of the (2-1)-th motor, wherein the second bracket rotates such that the upper case is tilted leftwards, through forward rotation driving of the (2-2)-th motor, and wherein the second bracket rotates such that the upper case is tilted rightwards, through reverse rotation driving of the (2-2)-th motor.

14. A non-transitory computer recording medium coupled to a computer that is hardware, and in which a program for executing the method of claim 8 is stored.

\* \* \* \* \*